US00PP27933P2

(12) United States Plant Patent
Couturieux

(10) Patent No.: US PP27,933 P2
(45) Date of Patent: Apr. 25, 2017

(54) ***SPIRAEA* PLANT NAMED 'COURISPI01'**

(50) Latin Name: *Spiraea betulifolia*
Varietal Denomination: COURISPI01

(71) Applicant: Jacques Couturieux, Moyenmoutier (FR)

(72) Inventor: Jacques Couturieux, Moyenmoutier (FR)

( * ) Notice: Subject to any disclaimer, the term of this patent is extended or adjusted under 35 U.S.C. 154(b) by 219 days.

(21) Appl. No.: 14/544,272

(22) Filed: Dec. 16, 2014

(51) Int. Cl.
*A01H 5/02* (2006.01)

(52) U.S. Cl.
USPC ..... Plt./226

(58) Field of Classification Search
USPC ..... Plt./226
CPC ..... A01H 5/02
See application file for complete search history.

*Primary Examiner* — Kent L Bell
(74) *Attorney, Agent, or Firm* — Penny J. Aguirre

(57) ABSTRACT

A new cultivar of *Spiraea betulifolia*, 'COURISPI01', that is characterized by compact plant habit, its flowers that are pink in color, and its re-blooming habit.

2 Drawing Sheets

Botanical classification: *Spiraea betulifolia.*
Variety denomination: 'COURISPI01'.

BACKGROUND OF THE INVENTION

The present invention relates to a new and distinct cultivar of *Spiraea*, botanically known as *Spiraea betulifolia* 'COURISPI01' and will be referred to hereafter by its cultivar name, 'COURISPI01'. 'COURISPI01' is a new variety of *Spiraea* for landscape use.

The new cultivar is the result of a controlled breeding program conducted by the Inventors in Moyenmoutier, France with the goal of developing new cultivars of *Spiraea betulifolia* with compact plant habits. The new cultivar arose from repeated selections by collecting open pollinated seed in three rounds of selections of proprietary seedlings from 2005 to 2007. The male is unknown.

Asexual propagation of the new cultivar was first accomplished by the Inventor by softwood stem cuttings in 2012 in Moyenmoutier, France. Asexual propagation of the new cultivar by softwood stem cuttings has determined that the characteristics of the new cultivar are stable and are reproduced true to type in successive generations

SUMMARY OF THE INVENTION

The following traits have been repeatedly observed and represent the characteristics of the new cultivar. These attributes in combination distinguish 'COURISPI01' as a new and unique cultivar of *Spiraea.*

1. 'COURISPI01' exhibits a compact plant habit.
2. 'COURISPI01' exhibits flowers that are pink in color.
3. 'COURISPI01' exhibits re-blooming habit; flowering in May and re-blooming in August in France.

The female parent of 'COURISPI01', an unnamed proprietary seedling of *Spiraea betulifolia* differs from 'COURISPI01' in having a more compact plant habit, in having smaller flowers that are lighter pink in color, and lacking a re-blooming habit. Typical plants of the species *Spiraea betulifolia* exhibit white flowers. 'COURISPI01' can also be compared to *Spiraea betulifolia* cultivars including 'Tor' (not patented) and 'Tor Gold' (not patented). Both 'Tor' and 'Tor Gold' differ from 'COURISPI01' in having flowers that are white in color, in having less compact and taller plant habits, and in lacking a re-blooming. In addition, 'Tor Gold' exhibits yellow-green foliage.

BRIEF DESCRIPTION OF THE DRAWINGS

The accompanying colored photographs illustrate the overall appearance and distinct characteristics of the new *Spiraea*. The photographs were taken of a plant two years in age as grown in a trial garden in Moyenmoutier, France.

The photograph in FIG. 1 provides a view of the overall plant habit of 'COURISPI01' in bloom.

Figure 1:
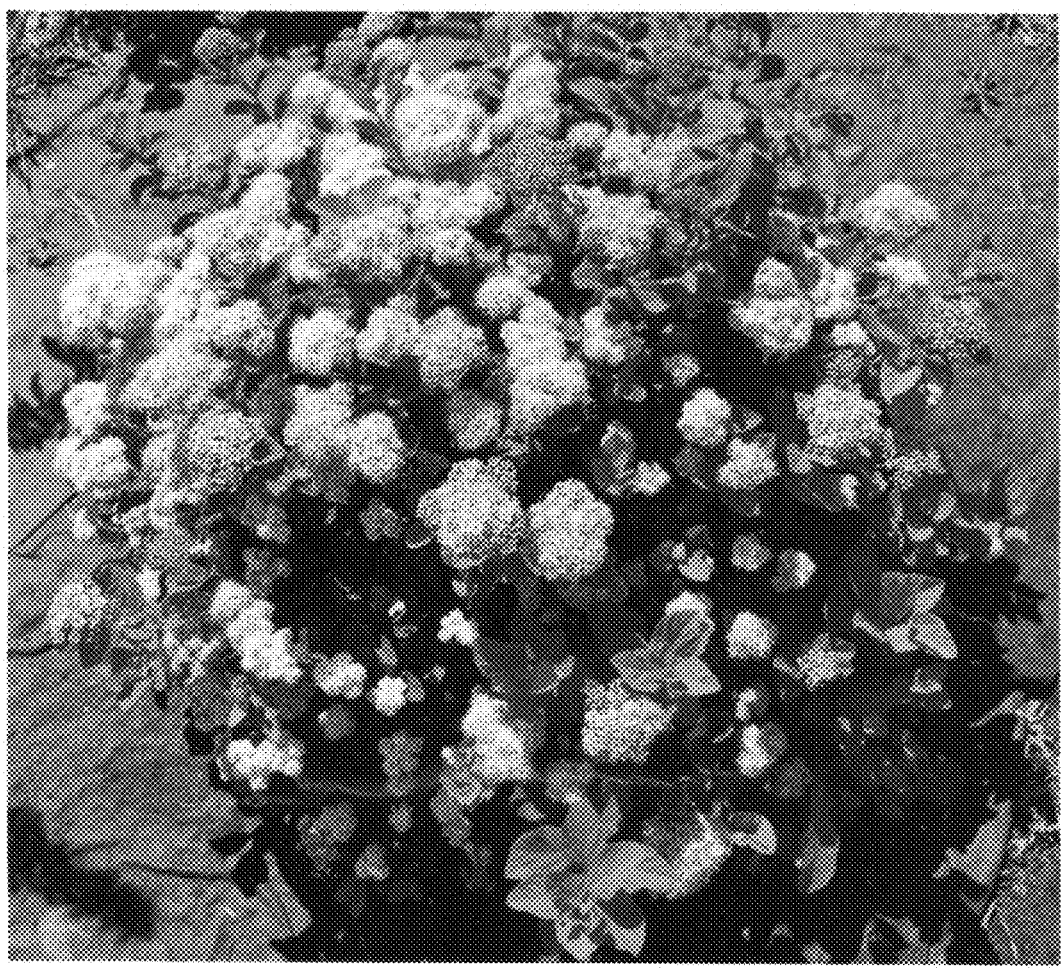
Figure 2:
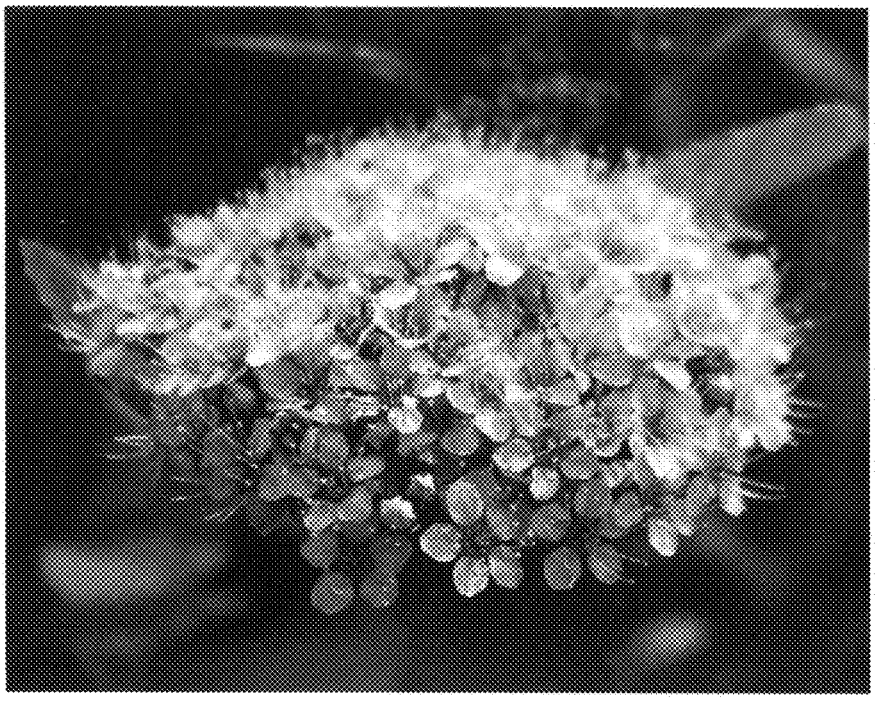

The photograph in FIG. 2 provides a close-up view of an inflorescence of 'COURISPI01'.

Figure 3:
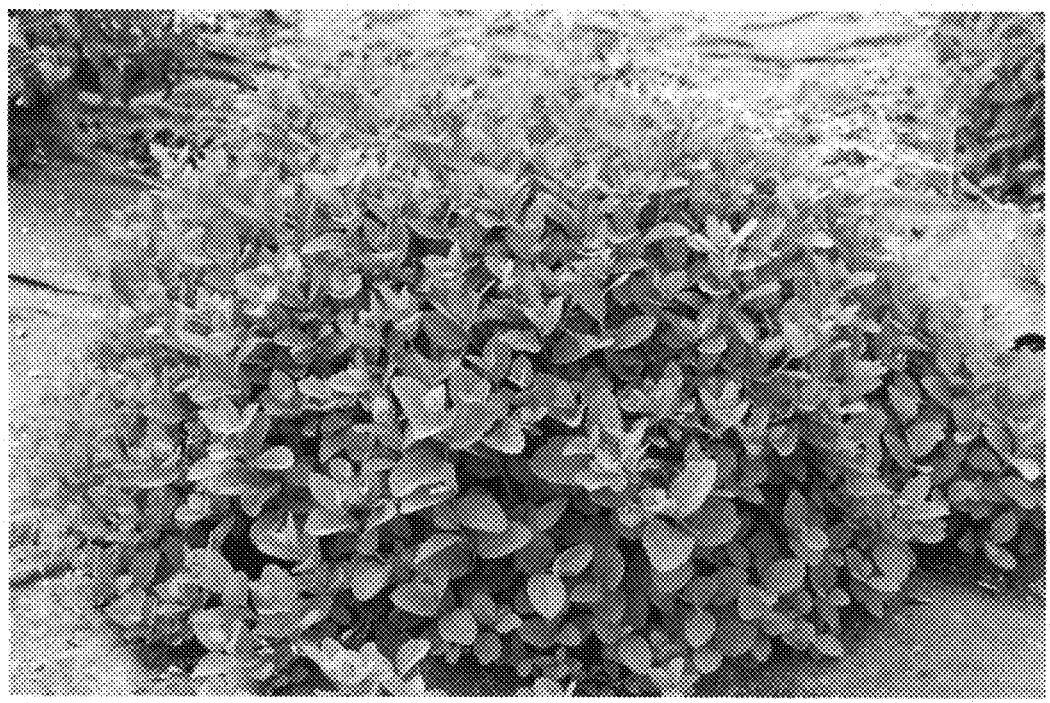

The photograph in FIG. 3 provides a close-up view of the spring foliage of 'COURISPI01'.

The colors in the photographs are as close as possible with the digital photography techniques available, the color values cited in the detailed botanical description accurately describe the colors of the new *Spiraea.*

DETAILED BOTANICAL DESCRIPTION

The following is a detailed description of one year-old plants of the new cultivar as grown outdoors in two-gallon containers in St. Paul, Minn. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming period.*—Initially blooms in May followed by a second bloom period in August, in France.

*Plant type.*—Deciduous shrub.

*Plant habit.*—Compact, mounded.

*Height and spread.*—Reaches an average of 55 cm in height and 80 cm in width.

*Hardiness.*—At least in U.S.D.A. Zones 3 to 8.

*Diseases.*—No unique susceptibility or resistance to diseases has been observed.

*Root description.*—Fibrous and fine.

*Propagation.*—Softwood stem cuttings.

*Growth rate.*—Moderate.

Stem description:

*Shape.*—Oval to rounded.

*Stem color.*—New growth; 145A in spring and becoming 145B and suffused with 187A in summer, mature wood; a blend of 177A and 200A.

*Stem size.*—Main stems; an average of 12 cm in length and 7 cm in width, lateral branches; an average of 15 cm in length and 3 mm in width.

*Stem strength.*—Strong.

*Stem surface.*—New growth; shiny and smooth, mature wood; bark-like but fairly smooth.

*Internode length.*—An average of 3 cm.

*Branching.*—An average of 6 lateral branches per main stem, stems held upright to an angle ranging between 20° (middle area) to 40° (outer area) to the main stem.

Foliage description:

*Leaf shape.*—Oval.

*Leaf division.*—Simple.

*Leaf base.*—Acute.

*Leaf apex.*—Obtuse.

*Leaf fragrance.*—None.

*Leaflet venation.*—Pinnate, color on upper and lower surface on young leaf matches leaf color, color of upper surface on mature leaf is 161A with a slight overlay of N34A, color on lower surface of mature leaf 137C suffused with an overlay of 179A.

*Leaflet margins.*—Serrated.

*Leaf arrangement.*—Alternate.

*Leaf attachment.*—Petiolate.

*Leaf surface.*—Upper surface; glabrous and satiny, lower surface; glabrous and dull.

*Leaf size.*—Average of 4 cm in length and 3 cm in width.

*Leaf quantity.*—Average of 16 on a branch 15 cm in length.

*Leaf color.*—Spring upper and lower surface; 145A to 145B, summer upper and lower surface; 137C, fall upper surface; 146A and suffused with 184A especially at the margins, fall lower surface; 144A and suffused with 184A especially at the margins.

*Petioles.*—Up to 3 mm in length and 1.2 mm in width, spring and summer color; 145B to 145C and suffused with 186B, fall color; 161A and suffused with 184A and 46B, glabrous and satiny surface.

*Stipules.*—Glandular-like, an average of 2 mm in length and 1 mm in diameter, dull, flaky surface, 161C in color with some suffused with 184A.

Inflorescence description:

*Inflorescence type.*—Dense umbellate corymbs, present at terminus of lateral branches.

*Inflorescence size.*—About 4 cm in diameter and 2 cm in depth.

*Peduncles.*—About 1 cm in length and 0.5 mm in width, 144B in color, glabrous surface.

*Pedicels.*—An average of 5 mm in length and 0.3 mm in width, 144B in color, glabrous surface.

*Flower buds.*—Globose in shape, 2.5 mm in depth and diameter, a blend of 75A and 76D and color.

*Flower fragrance.*—None.

*Persistence of flowers.*—Calyx persistent.

*Flower quantity.*—Average of 100 per inflorescence.

*Lastingness of flowers.*—Each inflorescence lasts about 10 days with individual flowers lasting about 2 days.

*Flower type.*—Rotate with numerous extended stamens.

*Flower aspect.*—Inflorescence held upright on stem terminus.

*Flower size.*—About 6 mm in diameter and 5 mm in depth.

*Petals.*—5, about 2 mm in length and width, un-fused, orbicular in shape, rounded base and apex, glabrous surface, upper and lower surface 75A to 75B in color when opening, upper and lower surface when fully open a blend of 75C to 75D and 76D, not persistent.

*Calyx.*—Cone-shaped with flared tips, about 3 mm in width and 1.5 mm in depth.

*Sepals.*—5, tips are about 1.5 mm in width and depth, fused base, ovate in shape, entire margins with fine hairs, acute apex, upper and lower surface is 183B in color.

Reproductive organs:

*Pistils.*—5, style; 2 mm in length and 75C to 75D in color, stigmas; 0.3 mm in diameter, 75C in color, ovaries; superior, oblong in shape, 0.6 mm in length and 0.2 in width, 154C in color.

*Stamens.*—About 20, showy filaments; up to 6 mm in length and 76C in color, anthers; 0.3 mm in diameter, about 75C, pollen; moderate in quantity, 155D in color.

*Fruit and seed.*—None observed.

It is claimed:

1. A new and distinct cultivar of *Spiraea* plant named 'COURISPI01' as herein illustrated and described.

* * * * *